US005607429A

United States Patent [19]

Hayano et al.

[11] Patent Number: 5,607,429
[45] Date of Patent: Mar. 4, 1997

[54] WIRE FASTENING TOOL

[75] Inventors: Kijuro Hayano, 3959-1, Tamagawa, Chino-shi, Nagano-ken; Haruo Ajiro, Koshigaya, both of Japan

[73] Assignee: Kijuro Hayano, Japan

[21] Appl. No.: 287,671

[22] Filed: Aug. 8, 1994

[30] Foreign Application Priority Data

Aug. 9, 1993 [JP] Japan .................................. 5-216952
Sep. 21, 1993 [JP] Japan .................................. 5-257716

[51] Int. Cl.⁶ .................................................. A61B 17/82
[52] U.S. Cl. ............................ 606/74; 606/103; 24/136 K
[58] Field of Search ............................ 606/74, 232, 151, 606/103, 60, 72; 24/136 R, 136 K, 115 G; 140/93 D

[56] References Cited

U.S. PATENT DOCUMENTS

| 1,141,977 | 6/1915 | Rogers | 24/136 R |
|---|---|---|---|
| 1,388,045 | 8/1921 | Johnson | 24/136 R |
| 2,780,794 | 2/1957 | Cresson . | |
| 3,698,047 | 10/1972 | Pierce | 24/136 R |
| 4,473,102 | 9/1984 | Ohman et al. | 24/136 K |
| 4,923,471 | 5/1990 | Morgan . | |
| 4,966,600 | 10/1990 | Songer et al. . | |
| 5,376,101 | 12/1994 | Green et al. | 606/232 |

FOREIGN PATENT DOCUMENTS

| 2911748 | 10/1980 | Germany | 606/74 |
|---|---|---|---|
| 4156837 | 5/1992 | Japan . | |

OTHER PUBLICATIONS

Patent Abstracts of Japan, vol. 16, No. 443 (C-0985) 29 May 1992.

*Primary Examiner*—Guy V. Tucker
*Attorney, Agent, or Firm*—Dorn, McEachran, Jambor & Keating

[57] ABSTRACT

A wire fastening tool has a wire mounting portion on which one end of a wire is to be mounted, a containing portion into which a movable member is to be inserted from outside and removably contained, and at least two openings which are formed in a peripheral wall forming the containing portion and into which the other end of the wire is to be inserted. The movable member is inserted with the other end of the wire passed through the openings and inserted in the containing portion, whereby the wire is bent between the movable member and the containing portion and is pressed between the outer surface of the movable member and the inner surface of the containing portion.

5 Claims, 4 Drawing Sheets

WIRE FASTENING TOOL

BACKGROUND OF THE INVENTION

1. Field of the Invention

This invention relates to a wire fastening tool for fastening a wire, and particularly to the structure of a fastening tool suitable for fastening the opposite ends of a metallic wire when supporting and fixing fractured bone portions or re-fixing broken bones.

2. Related Background Art

Heretofore, when fractured bone portions are to be tied together or when after a portion of a bone was cut off for some reason or other, the cut-off portion is to be again fixed at its original position, it has been the practice to pass a wire for a living body through an insertion hole formed in the bone or put a wire for a living body around the body to thereby bind up the wire, and fasten the opposite ends of this wire to thereby fix the broken-away portion of the bone. The fastening of the wire is accomplished by once tying up the wire tightly, and then wrenching the opposite ends of the wire together.

As the wire for a living body, use is often made of a single wire of stainless steel, Co—Cr—Mo alloy or the like. However, these wires have suffered from problems in terms of corrosion resistance and fitness to a living body and moreover, have had a disadvantage that when MRI (magnetic resonance image pickup method) is used, image pickup is hampered by the halation caused by the wire.

On the other hand, in recent years, use has also been made of wires of pure titanium or titanium alloys having good corrosion resistance and good fitness to a living body. These wires have a feature that they do not cause halation to an electromagnetic wave and moreover, when they are used with artificial bones or artificial dental roots made of titanium or a titanium alloy which have recently used, the wires used are the same metal as these and therefore, electrochemical corrosion occurring between different metals can be avoided.

However, the wires of titanium, as compared, for example, with wires of stainless steel, merely have a fraction of ductility and a little over half of tensile strength and therefore, unless the wire fastening work is done carefully, the wrenched-together portions of the wires may be broken away. Accordingly, there have been cases where during a surgical operation, sufficient tying-up or wrenching together cannot be done from the fear against the breakage of the wire and precise fixing of bone tissue cannot be accomplished.

So, for example, in Japanese Laid-Open Patent Application No. 4-156837, it is described to insert two wires into a metal fitting of titanium having a U-shaped or otherwise shaped opening, and caulk and fix the metal fitting and the wires. According to this metal fitting, the wires need not be tightly wrenched together and thus, the possibility of the wires being broken away can be reduced.

However, said metal fitting is formed into a channel of U-shaped, V-shaped or otherwise shaped cross-section provided with a wire insertion opening, and this leads to a problem that the wires cannot be sufficiently supported when the wires are tied up while being inserted in the metal fitting.

Also, a plurality of wires are simply caulked and fixed and therefore, to obtain a sufficient fastening force, it is necessary to partially strongly press the metal fitting to such a degree that a recess is formed in the outer surface portion of the metal fitting, and to a cause the wires to eat into the metal fitting with the inner surface of the metal fitting and the wires deformed into an uneven shape. Accordingly, the strength of the caulking must be suitably adjusted, and if the caulking is weak, the fastened portion may come off, and if the Caulking is too strong, the wires may be broken away.

SUMMARY OF THE INVENTION

It is an object of the present invention to solve the above-noted problems peculiar to the prior art and to provide a fastening tool which does not cause the breakage of a wire during the fastening of the wire.

It is a further object of the present invention to provide a fastening tool which readily enables wire tie-up work to be accomplished.

It is still a further object of the present invention to provide a fastening tool which can provide a substantially constant wire fastening force irrespective of the manner of operation.

It is yet still a further object of the present invention to increase the wire fastening force without causing the risk of breaking away the wire.

It is another object of the present invention to prevent the surrounding tissue from being injured when a fastening tool having fastened a wire has been embedded in a living body.

It is still another object of the present invention to provide a fastening tool which can fasten a wire and also can cut an unnecessary wire.

The wire fastening tool of the present invention has a wire mounting portion on which one end of a wire is mounted, a containing portion into which a movable member is inserted and is removably contained, and at least two openings for the wire into which the other end of the wire is inserted and which is formed in a peripheral wall forming said containing portion, and is designed such that said movable member is inserted with the other end of the wire inserted in said containing portion through said two openings for the wire, whereby the wire is bent between said movable member and said containing portion and is pressed between the outer surface of said movable member and the inner surface of said containing portion.

Other objects of the present invention will become apparent from the following detailed description taken in conjunction with the accompanying drawings.

DESCRIPTION OF THE PREFERRED EMBODIMENTS

An embodiment of a wire fastening tool according to the present invention will now be described with reference to the drawings. The present embodiment is for fastening a wire for a living body which is made of a titanium alloy as a material, and is comprised of a fastening member 1 shown in FIGS. 3 and 4, and a movable shaft member 2 shown in FIGS. 5 and 6. These members are formed of a titanium alloy similar to the material of the wire for a living body, for example, Ti-6A1-4V alloy.

Figure 3:
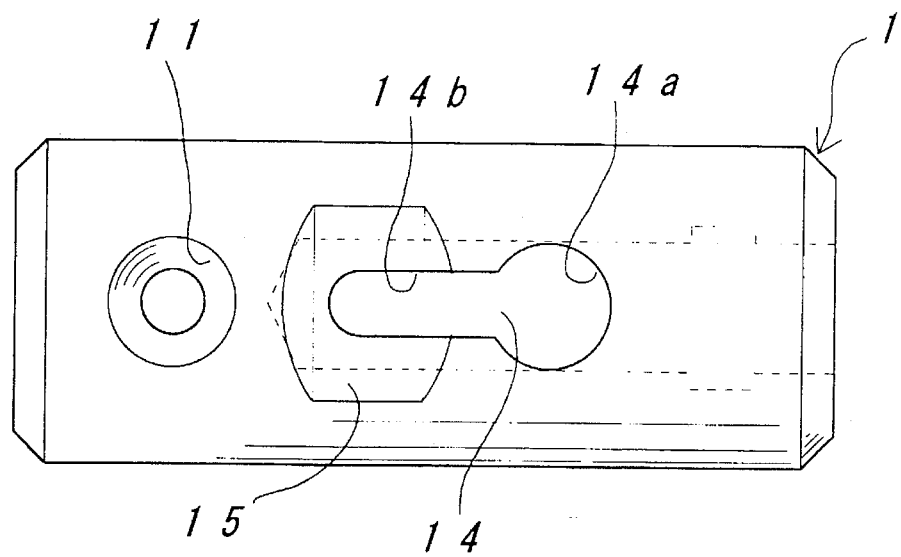
FIG. 3 is a plan view of a fastening member in the same embodiment.
Figure 4:
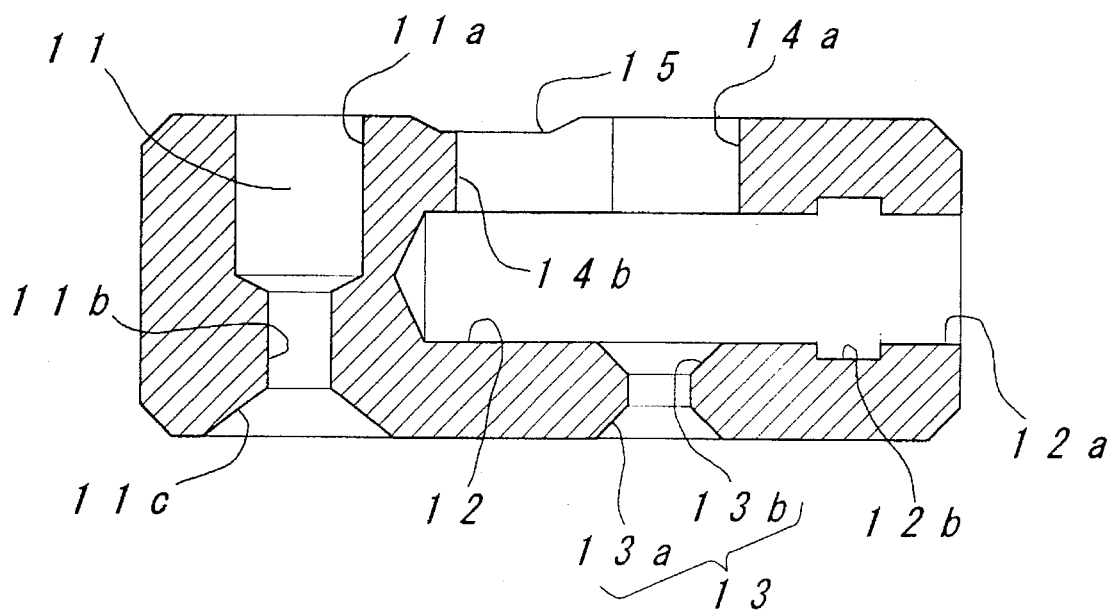
FIG. 4 is a longitudinal cross-sectional view of the fastening member in the same embodiment.

Referring to FIGS. 3 and 4, the fastening member 1 is formed into a substantially cylindrical shape, and has a wire mounting hole 11 vertically formed in the left end portion thereof, a shaft containing aperture 12 formed horizontally from the right end surface thereof, and openings 13 and 14 formed in the peripheral wall of the shaft containing aperture 12 in substantially opposed relationship with each other.

The wire mounting hole 11 has a large-diametered portion 11a provided on the upper surface side thereof, a small-diametered portion 11b connected to the large-diametered portion 11a with a level difference portion interposed therebetween and having a diameter slightly larger than the diameter of the wire, and an enlarged diameter portion 11c provided on the bottom surface side and formed into a tapered shape so as to increase its diameter downwardly. An annular groove 12b is formed on the inner surface of the shaft containing aperture 12 which is adjacent to the inlet port 12a thereof.

The opening 13 has an outer enlarged diameter portion 13a formed on the bottom surface side and an inner enlarged diameter portion 13b facing the shaft containing aperture 12, and an equal-diametered portion of a slight length is provided between the portions 13a and 13b.

On the other hand, the opening 14 has a round hole portion 14a of substantially the same diameter as the maximum diameter of the opening 13, and a slot portion 14b extending from the round hole portion 14a axially of the shaft containing aperture 12. The outer edge portion around the left end portion of the slot portion 14b provides an open edge recess 15 retracted from the cylindrical outer surface of the fastening member 1.

Figure 5:
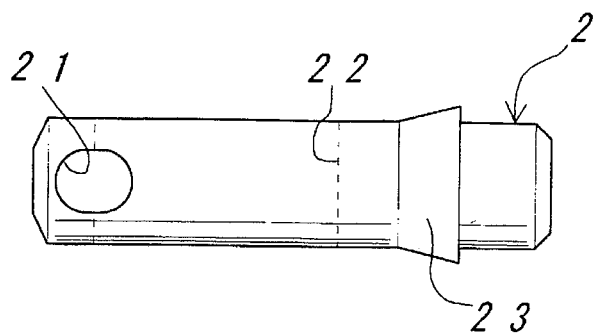
FIG. 5 is a plan view of a movable shaft member in the same embodiment.
Figure 6:
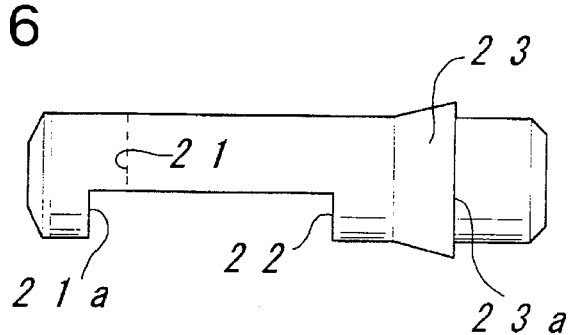
FIG. 6 is a longitudinal side view of the movable shaft member in the same embodiment.

On the other hand, as shown in FIGS. 5 and 6, the movable shaft member 2 is formed into the shape of a round shaft, and is formed with a wire insertion hole 21 on the fore end side thereof and a concave groove portion 22 on one side of the peripheral surface thereof. A cut-off portion 21a is formed in the wire insertion hole 21 due to the presence of the concave groove portion 22 so that the wire insertion hole 21 and the concave groove portion 22 are continuous to each other. An annular inclined surface portion 23 is provided on the outer peripheral surface of the movable shaft member 2 near the right end thereof, and a level difference 23a is formed at the right of the annular inclined surface portion 23.

Figure 7:
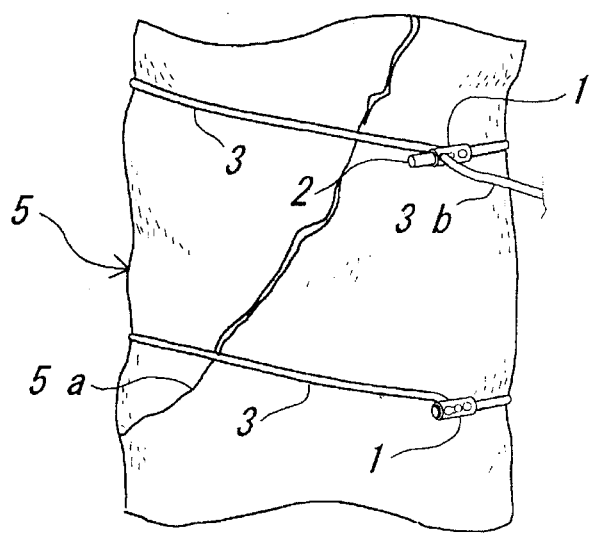
FIG. 7 is a perspective view showing a state in which a wire for a living body has been fastened by the use of the same embodiment.

FIG. 7 shows a state in which the wire 3 of titanium alloy for a living body is passed over a bone 5 in such a manner as to cross the joint line 5a of the bone 5 and the opposite ends of the wire 3 for a living body are fastened together by the fastening member 1 and movable shaft member 2 of the present embodiment. The procedure until such fastening is accomplished will now be described with reference to FIGS. 1 and 2.

Figure 1:
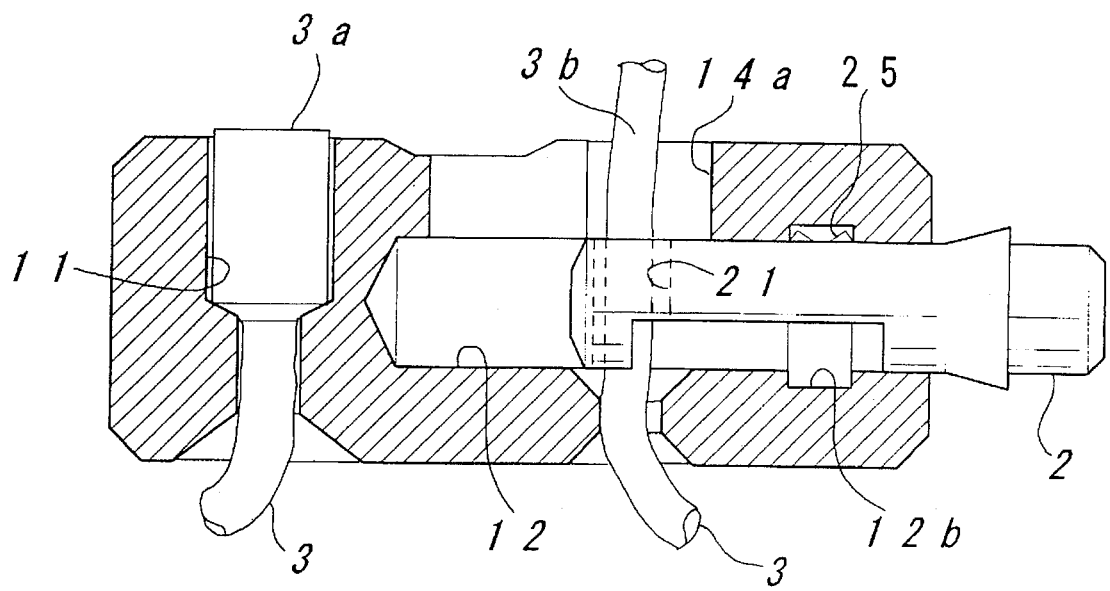
FIG. 1 is a cross-sectional view showing the state of a wire before fastened to show the fastening operation of an embodiment of a wire fastening tool according to the present invention.

First, as shown in FIG. 1, a large-diametered head 3a is formed on one end of the wire 3 for a living body, and the wire 3 for a living body is inserted into the wire mounting hole 11 and the head 3a is restrained by the level difference portion of the wire mounting hole 11. Subsequently, the movable shaft member 2 is inserted into the shaft containing aperture 12 and adjustment is made such that the axis of the wire insertion hole 21 substantially coincides with the opening 13 in the fastening member 1 and the round hole portion 14a. Since the round hole portion 14a is formed with a larger diameter than the wire insertion hole 21, the movable shaft member 2 can be positionally adjusted by visual observation to thereby readily bring the wire insertion hole 21 into coincidence with the round hole portion 14a. The wire 3 for a living body after wound on the bone tissue is then inserted into the opening 13, the wire insertion hole 21 and the round hole portion 14a, and the other end portion 3b of the wire 3 for a living body is drawn out upwardly, whereafter the other end portion 3b is pulled to thereby bring about a state in which the wire 3 for a living body has been tightened.

Figure 2:
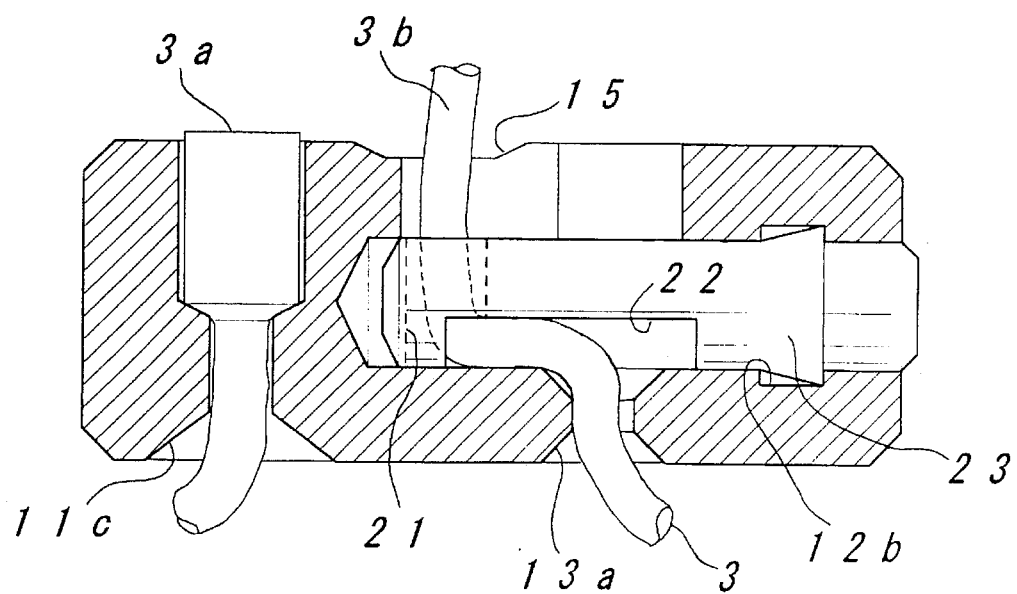
FIG. 2 is a cross-sectional view showing the state of the wire after fastened to show the fastening operation of the embodiment of the wire fastening tool according to the present invention.

When in this state, the movable shaft member 2 is pushed into the shaft containing aperture 12, the wire 3 for a living body is drawn into the shaft containing aperture 12, as shown in FIG. 2. When the movable shaft member 2 has been fully pushed into the shaft containing aperture 12, the wire 3 for a living body extends along the concave groove portion 22 and becomes bent at the inner inlet portion of the opening 13 and the cut-off portion 21a of the wire insertion hole 21. In the course of movement of the movable shaft portion 2 into the inner part of the shaft containing aperture 12, the inclined surface portion 23 of the movable shaft member 2 comes into the shaft containing aperture 12 and therefore, more or less insertion resistance is felt, but when the movable shaft member 2 is pushed in against this insertion resistance, the inclined surface portion 23 comes into coincidence with the large-diametered portion 12b and the movable shaft member 2 is reliably restrained by the level difference 23a.

The enlarged diameter portion 11c and the outer enlarged diameter portion 13a are formed in the wire mounting hole 11 and the opening 13, respectively, on the bottom sides thereof so that the wire can be sufficiently bent under the bottom surface of the fastening member 1 when the wire is fastened, and the wire fastening tool can be tightly fixed to the surface of the bone. When it is desired to bring the wire fastening tool into more intimate contact with the surface of the bone, there may be provided a concave groove portion on the bottom surface formed continuously from the enlarged diameter portion 11c of the wire mounting hole 11 or the enlarged diameter portion 13a of the opening 13 to the left or right end portion of the fastening member 1. The inner enlarged diameter portion 13b of the opening 13, like the outer enlarged diameter portions 11c and 13a, enables the drawn-in wire for a living body to be bent at a small radius of curvature.

The other end 3b of the wire for a living body fastened as described above protrudes from the slot portion 14b of the opening 14 and is therefore severed after the fastening work. If at this time, the wire for a living body is severed just above the slot portion 14b, the severed end portion of the wire will not protrude above the outer peripheral surface of the fastening member 1 and therefore will not injure the surrounding tissue after the wire is embedded in the body.

The concave groove portion 22 formed in the movable shaft member 2 is formed to a depth substantially equal to the diameter of the wire and thus, the wire 3 for a living body is bent on the front and rear sides of the portion thereof contained in the concave groove portion 22 and also is pressed between the surface of the concave groove portion 22 and the inner surface of the shaft containing aperture 12 chiefly near the bent portion. Accordingly, the wire can be fastened firmly and reliably, although even when the concave groove portion 22 is formed somewhat more deeply than the diameter of the wire, said pressing effect will not entirely-disappear because the wire is bent in the front and rear portions thereof.

However, when it is desired to fasten the wire more firmly, the depth of the concave groove portion 22 can be made slightly shallower than the diameter of the wire (e.g. a depth of 0.9 mm or less relative to the diameter 1.0 mm of the wire) and also the width of the concave grove portion 22 can be made greater than the diameter of the wire or as in the present embodiment, the concave groove portion can be made into a widthwisely open shape to thereby vary the cross-sectional shape of the wire by pressure with the movement of the movable shaft member 2. A variation in the cross-sectional shape of the wire increases the holding force of the wire in the concave groove portion 22 and also greatly increase the fastening action provided by the bending of the wire. In this case, conversely the width of the concave groove portion 22 may be narrowed and the depth thereof may be made greater than the diameter of the wire.

With these actions taken into account, the depth of the concave groove portion 22 is suitable set in conformity with the spacing between the two bent portions of the wire. The spacing between the bent portions depends on the shape of the concave Groove portion 22, but to reduce the amount of localized deformation of the wire and yet effect fastening reliably, said spacing may preferably be about three times as Great as the diameter of the wire.

As described above, in the present embodiment, the wire is fixed by bending and resultant pressure, and even if the angle of bend and the amount of pressure of each portion of the wire are not made Great, a sufficient fastening force could be secured. Accordingly, it is not necessary to apply localized pressure to the wire to thereby form an eat-in portion as in the prior art and therefore, there is very little possibility of the wire being broken away.

Further, in the point that a great force is not required in the fastening operation and fastening is completed by one action, the effect of the operability is noted. Moreover, the tool need not be inserted for the purpose of wrenching or caulking the wire and therefore, the opening portion of the body surface can be made small during a surgical operation.

The fastening force depends only on the shapes of the movable shaft member and fastening member and therefore, as compared with the prior art in which during the fastening operation, the work was done while adjusting the fastening force in fear of the breakage of the wire, the working property is markedly improved.

In the present embodiment, the fastening member and movable shaft member are of a cylindrical shape, but alternatively, they may be of different shapes, for example, of a thin plate-like shape, and particularly, the fastening member may preferably be made into a shape in which the bottom surface matches the surface of the bone and the upper surface is smooth.

Also, in the present embodiment, the movable shaft member is pushed in to thereby fasten the wire, but design may be made such that the movable shaft member is drawn out to thereby bring about the fastened state.

In the present embodiment, the inclined surface portion 23 and the large-diametered portion 12b are fitted together to thereby hold the movable shaft member in its fastening position, but actually, when the movable shaft member is once pushed in to bring the wire into the bent state as shown in FIG. 2, the movable shaft member 2 will become unable to be drawn out due to the resistance of the wire even if this holding means is absent. Accordingly, the holding means in the fastened state is not always necessary.

In FIG. 1, there is shown a projection 25 for positioning the movable shaft member 2 when the wire is passed through the opening 13, the wire insertion hole 21 and the opening 14. This projection 25 fits into the annular groove 12b so as to bring the wire insertion hole 21 into coincidence with the openings 13, 14, thereby prescribing the insertion depth of the movable shaft member 2. This projection 25 is formed so as to have such a degree of slight amount of protrusion that will provide light resistance during the insertion of the movable shaft member 2, or is formed of readily deformable plastic resin or the like.

To prescribe the angle about the axis during the insertion of the movable shaft member 2, a convex ridge and a concave groove extending in the axial direction (the direction of insertion) may be provided on the surfaces of the movable shaft member 2 and shaft containing aperture 12 and these may be slidably fitted together.

The movable portion (movable shaft member) need not be inserted in the containing portion (shaft containing aperture) as is done in the above-described embodiment, but may be, for example, of such structure that the movable portion is subsumed within the containing portion and an arm for driving the movable portion has been taken out of a discretely formed opening. Also, if possible in terms of material, the movable portion connected to the main body may be designed for movement by bellows or the like.

It is apparent that if use is made of U-shaped, V-shaped or otherwise shaped grooves having openings in the sides thereof, instead of the wire mounting hole, the opening for the wire, the wire insertion hole, the shaft containing aperture etc. in the above-described embodiment, an effect similar to that described above will be attained. The wire insertion hole 22 formed in the movable shaft member 2 is not always necessary, but even if design is made such that the wire inserted in the shaft containing aperture is pushed into the tip 10 end portion of the movable shaft member, it will be possible to fasten the wire as shown in FIG. 2.

Figure 8:
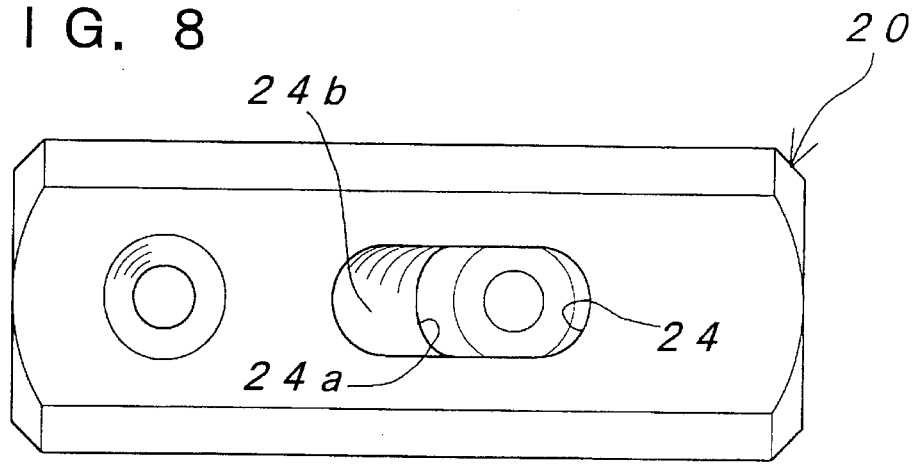
FIG. 8 is a plan view of a fastening member for showing the structure of another embodiment of the present invention.
Figure 9:
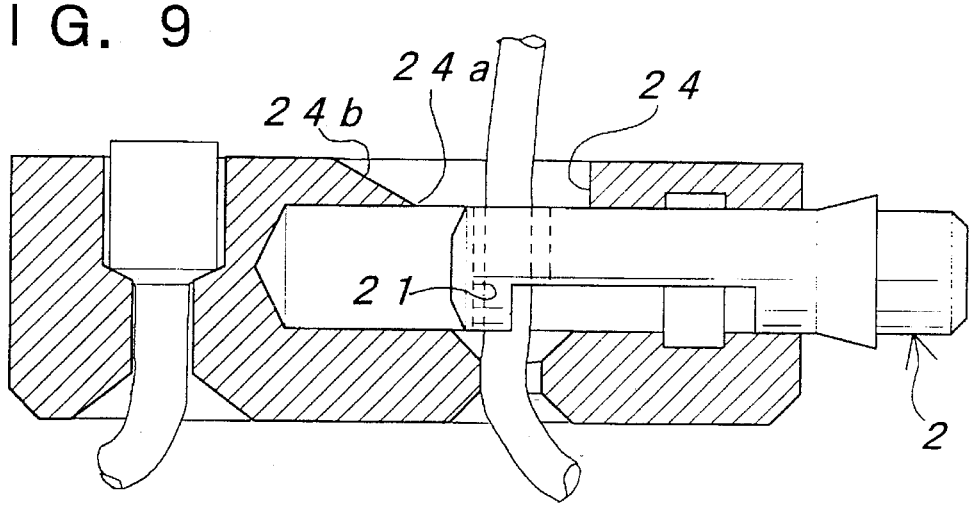
FIG. 9 is a longitudinal cross-sectional view showing the state of a wire before fastened in the wire fastening operation.
Figure 10:
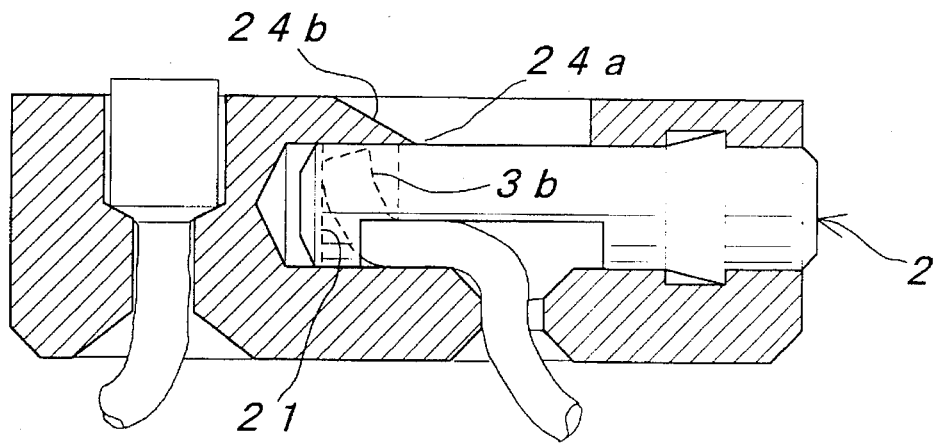
FIG. 10 is a longitudinal cross-sectional view showing the state of the wire after fastened.

A more preferred embodiment of the present invention will now be described with reference to FIGS. 8, 9 and 10. As shown in FIG. 8, the basic structure of this embodiment is similar to the above-described embodiment, but a fastening member 20 is formed with an opening of a different shape instead of the opening 14. The opening 24 is formed as a generally oval through-hole, and the inner peripheral surface 24b of the opening 24 which is formed in the inner part of the shaft containing aperture 12 is formed into an inclined curved surface to thereby make the lower edge line thereof sharp so as to form a cutting blade 24a. This cutting blade 24a is formed so as to be opposed to the direction of movement of the movable shaft member 2 into the shaft containing aperture 12 and therefore, when as shown in FIG. 9, the movable shaft member 2 having the wire 3 for a living body inserted therein is pushed into the shaft containing aperture 12, the root of the wire 3 protruding from the wire insertion hole 12 is cut by the cutting blade 24a, and as shown in FIG. 10, the tip end of the wire 3 is contained in the wire insertion hole 21.

As described above, in the present embodiment, the cutting of the tip end of the wire automatically takes place simultaneously with the fastening of the wire 3 for a living body, and the cutting of the excess portion of the wire need not be done discretely.

The edge of the cutting blade 24a is formed so as to be arcuate as viewed in a plan view thereof, and can cut the wire 3 for a living body with a small stress and reliably. The tip end portion 3b of the cut wire 3 for a living body is contained in the wire insertion hole 21, and the upper opening of the wire insertion hole 21 is fully covered with the side wall of the shaft containing aperture 12 located on the back side of the cutting blade 24a. Also, the cutting blade 24a itself comes into substantially perfect contact with the outer peripheral surface of the movable shaft 2 and therefore, the sharp portion of the edge of the cutting blade does not injure the surrounding tissue and the operator.

The cutting blade 24a in this embodiment can be easily made by initially forming the opening 24 to a small size, and obliquely cutting the left edge portion of the opening 24 by means of an end mill or the like. If the cutting blade 24a is formed in this manner, no other part will be required and therefore, the downsizing of the fastening tool itself will not be hampered. Of course, after the formation of the opening 24, a discrete cutting blade may be attached to the outer or inner side of the edge of the opening so that the edge of the cutting blade may face the interior of the opening 24.

The foregoing two embodiments have been described with respect to an example of the fastening of a wire for a living body made of a titanium alloy, but the wire fastening tool of the present invention covers those for fastening not only a wire for a living body, but wires having various uses, and can be applied to not only metallic wires of titanium alloys but also wires of various materials such as synthetic resin.

Also, in the above-described embodiments, one of the openings is such a degree of opening that permits the insertion of the wire thereinto and the other opening is an opening extending in the direction of movement of the movable shaft, and the gap formed by the concave groove portion is formed only on the side of the other opening, but alternatively, both of the openings may be such a degree of openings that will permit the insertion of the wire thereinto, and the gap may be provided on both opening sides. In such case, the wire will be bent at total three locations, i.e., the inside of the opening on the wire inlet side and the both sides of the wire insertion hole (before the wire cutting on the draw-out side, total four locations, i.e., two locations inside the two openings and two locations on both sides of the wire insertion hole).

In such of the above-described embodiments, the wire mounting portion formed as a wire mounting hole is not restricted to the construction shown in the embodiments, but for example, the wire may be secured to a predetermined location on the fastening tool by welding or brazing, and further, as the structure of the wire mounting portion, the wire may be twined or fitted, whereafter a cap may be put thereon or a portion to be nipped by a clip may be formed.

What is claimed is:

1. A wire fastening device for securing body parts by means of a wire adaptable to a living body, said wire fastening device comprising:

a first member having a bore and first and second openings facing each other, said bore being located between said first and second openings, each of said openings having an area through which said wire can be inserted, said first opening being extended along said bore; and a second member disposed movably within said bore, said second member having a through-hole extended across the direction of movement of said second member and a recess formed on an outer portion of said second member to be extended along said bore, said through-hole and said recess communicating to pass said wire therethrough, and said through-hole and said recess being opposed to, respectively, said first opening and said second opening of said first member, said second member being movable within said bore and acting on said wire when said wire is passed through said openings and said through-hole, such that said wire is extended between a bottom surface of said recess and an inner surface of said first member defining said bore and is bent in a crank-like configuration and fastened thereby, said first member having a cutting blade for cutting said wire which faces one of said first and second openings, and an edge of said cutting blade is opposed to the direction of movement of said second member.

2. A wire fastening device according to claim 1, wherein a gap between said bottom surface of said recess and said inner surface of said first member defining said bore is smaller than the diameter of said wire.

3. A wire fastening device according to claim 1, wherein said inner surface of said first member defining said bore and an outer surface of said second member are provided with engagement elements for positioning each other at a location where said wire is bent and fastened.

4. A wire fastening device according to claim 1, wherein said inner surface of said first member defining said bore and an outer surface of said second member are provided with engagement elements for positioning each other at a location where said wire may be inserted into and passed through said first and second openings and said through-hole.

5. A wire fastening device according to claim 1, wherein said first member has a mounting hole formed in a manner permitting said wire to be inserted into and held therein.

* * * * *